United States Patent
Tchaga

(10) Patent No.: US 6,703,498 B2
(45) Date of Patent: Mar. 9, 2004

(54) WATER-SOLUBLE POLYMERIC METAL ION AFFINITY COMPOSITIONS AND METHODS FOR USING THE SAME

(75) Inventor: Grigoriy S. Tchaga, Newark, CA (US)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

(21) Appl. No.: 10/176,955

(22) Filed: Jun. 20, 2002

(65) Prior Publication Data

US 2003/0023037 A1 Jan. 30, 2003

Related U.S. Application Data

(60) Provisional application No. 60/300,336, filed on Jun. 21, 2001.

(51) Int. Cl.$^7$ ............... C08B 37/02; C08B 37/12; B01J 20/26
(52) U.S. Cl. ............... 536/112; 536/113; 536/121; 536/123.1; 556/117; 556/133; 556/134; 556/147; 556/176; 556/183; 562/553; 562/555
(58) Field of Search ............... 536/112, 113, 536/121, 123.1; 556/117, 133, 134, 147, 176, 183; 562/553, 555

(56) References Cited

U.S. PATENT DOCUMENTS

| | | | |
|---|---|---|---|
| 4,569,794 A | | 2/1986 | Smith et al. |
| 5,047,513 A | | 9/1991 | Dobeli et al. |
| 5,284,933 A | | 2/1994 | Dobeli et al. |
| 5,310,663 A | | 5/1994 | Dobeli et al. |
| 5,594,115 A | | 1/1997 | Sharma |
| 5,962,641 A | | 10/1999 | Nelson et al. |
| 5,990,289 A | * | 11/1999 | Fauquex et al. ............ 530/413 |
| 6,242,581 B1 | | 6/2001 | Nelson et al. |
| 6,365,147 B1 | * | 4/2002 | Luo et al. ................. 424/93.1 |
| 6,406,885 B1 | * | 6/2002 | Stewart et al. ............ 435/69.1 |
| 6,479,274 B1 | * | 11/2002 | Antalis et al. ............ 435/252.3 |
| 2002/0019496 A1 | | 2/2002 | Pevow |

OTHER PUBLICATIONS

Chaga et al. Natural Poly–Histidine Affinity Tag for Purification of Recombinant Proteins on Cobalt(II)–Carboxymethylaspartate Crosslinked Agarose. Journal of Chromatography A, 1999, 864, 247–56.*
E. Hochuli et al. "New metal chelate adsorbent selective for proteins and peptides containing neighbouring histidine residues" *Journal of Chromatography*, 411 (1987) 177–184.
Mantovaara et al. "Purification of human serum amyloid P component (SAP) by calcium affinity chromatography" *Biotechnology and Applied Biochemistry*, 11, 564–570 (1989).
Mantovaara et al. "Purification of Factor VIII: c coagulant activity from rat liver nonparenchymal cell culture medium by immobilized metal ion affinity chromatography" *Biotechnology and Applied Biochemistry*, 13, 120–126 (1991).
Porath et al. "Methal chelate affinity chromatography, a new approach to protein fractionation" *Nature*, vol. 258 Dec. 18, 1975.
Porath et al. "Immobilized metal ion affinity adsorption and immobilized metal ion affinity chromatography of biomaterials. Serum protein affinities for gel–immobilized iron and nickel ions" *Biochemistry*, (1988) 22, 1621–1630.
Porath et al. Review—"Immobilized metal ion affinity chromatography" *Protein Experssion and Purification*, 3, 26281 (1992).
Chaga et al. "A new method of synthesizing biopolymeric affinity" *Biotechnology Appl. Biochem.* (1997) 26, 7–14.
Chaga et al. "Immobilized metal ion affinity chromatography on Co2+– carboxymethylaspartate–agarose Superflow, as demonstrated by one–step purification of lactate dehydrogenase from chicken breast muscle" *Biotechnol Appl Biochem* (1999)29 19–24.
Mantovaara et al. "Further characterization of carboxymethylated Aspartic acid agaraose. Purification of Human a2–Macroglobulin and Hemopexin" *Biotechnology and Applied Biochemistry*, 13, 371–379 (1991).
Mantovaara et al. "Carboxymethylated aspartic acid agarose, a selective adsorbent for calcium–binding proteins, preliminary studies" *Biotechnology and Applied Biochemistry* 13, 315–322 (1991).

* cited by examiner

*Primary Examiner*—James O. Wilson
*Assistant Examiner*—Leigh C. Maier
(74) *Attorney, Agent, or Firm*—Bret E. Field; Bozicevic, Field & Francis

(57) ABSTRACT

Water-soluble metal ion affinity compounds and methods for using the same are provided. The subject compounds include an aspartate based metal chelating ligand bonded to a water-soluble polymeric substrate, where the ligand is complexed with a metal ion. In certain embodiments, the subject compounds further include a member of a signal producing system, e.g., a directly or an indirectly detectable label moiety. Also provided are water-insoluble supports having the subject compounds present on, e.g., immobilized on, at least one surface thereof. The subject compounds find use in a variety of different applications, including analyte detection and analyte purification applications.

23 Claims, No Drawings

WATER-SOLUBLE POLYMERIC METAL ION AFFINITY COMPOSITIONS AND METHODS FOR USING THE SAME

CROSS-REFERENCE TO RELATED APPLICATIONS

Pursuant to 35 U.S.C. § 119 (e), this application claims priority to the filing date of U.S. Provisional Patent Application Serial No. 60/300,336 filed Jun. 21, 2001; the disclosure of which is herein incorporated by reference.

INTRODUCTION

1. Field of the Invention

This invention relates generally immobilized metal ion affinity chromatography.

2. Background of the Invention

Immobilized Metal Ion Affinity Chromatography (IMAC) is one of the most frequently used techniques for purification of fusion proteins containing affinity sites for metal ions. IMAC is a separation principle that utilizes the differential affinity of proteins for immobilized metal ions to effect their separation. This differential affinity derives from the coordination bonds formed between metal ions and certain amino acid side chains exposed on the surface of the protein molecules.

Since the interaction between the immobilized metal ions and the side chains of amino acids has a readily reversible character, it can be utilized for adsorption and then be disrupted using mild (i.e., non denaturing) conditions. Adsorbents that are currently commercially available include iminodiacetic acid (IDA), nitriloacetic acid (NTA), caboxymethylated aspartic acid (CM-Asp), and triscarboxymethyl ethylene diamine (TED). These ligands offer a maximum of tri-(IDA), tetra-(NTA, CM-Asp), and pentadentate (TED) complexes with the respective metal ion.

In most commercially available adsorbents, metal chelating ligands are provided at an average density of about 12 Å. Depending on the ligand, various metals can be chelated. Metal ions typically used in IMAC procedures have been classified into three categories—hard, intermediate, and soft—based on their preferential reactivity toward nucleophiles. The hard metal ions $Fe^{3+}$, $Ca^{2+}$, and $Al^{3+}$ show a preference for oxygen; the soft metal ions $Cu^+$, $Hg^{2+}$, $Ag^+$, and the like show a preference for sulfur; and intermediate metal ions such as $Cu^{2+}$, $Ni^{2+}$, $Zn^{2+}$, and $Co^{2+}$ coordinate nitrogen, oxygen, and sulfur. The number of cysteine residues on the surfaces of proteins is limited; therefore, histidine residues are the major targets for intermediate metal ions.

Because of its commercial success, there is continued interest in the development of new "IMAC" technologies and applications. The present invention satisfies this need.

Relevant Literature

See U.S. Pat. Nos. 4,569,794; 5,047,513; 5,284,933; 5,310,663; 5,962,641; 5,594,115; and 6,242,581 as well as Chaga et al., Biotechnol. Appl. Biochem. (1997)26: 7–14. Also of interest are: Ford et al., Protein Expression and Purification (1991) 2:95–107; Hochuli, et al., J. Chromatography (1987) 411:177–184; Mantovaara et al., Biotechnology and Applied Biochemistry (1989) 11:564–570; Mantovaara et al., Biotechnology and Applied Biochemistry (1991) 13:315–322; Mantovaara et al., Biotechnology and Applied Biochemistry (1991) 13:120–126; Porath et al., Nature (1975) 258:598–599; Porath & Olin, Biochemistry (1983) 22:1621–1630; and Porath, J., Protein Purification and Expression (1992) 3:263–281.

SUMMARY OF THE INVENTION

Water-soluble metal ion affinity compounds and methods for using the same are provided. The subject compounds include an aspartate based metal chelating ligand bonded to a water-soluble polymeric substrate, where the ligand is complexed with a metal ion. In certain embodiments, the subject compounds further include a member of a signal producing system, e.g., a directly or an indirectly detectable label moiety. Also provided are water-insoluble supports having the subject compounds present on, e.g., immobilized on, at least one surface thereof. The subject compounds find use in a variety of different applications, including analyte detection and analyte purification applications.

Definitions

The terms "affinity peptide," "high affinity peptide," and "metal ion affinity peptide" are used interchangeably herein to refer to a histidine-rich peptide that binds to a metal ion.

The terms "protein of interest" and "fusion partner polypeptide," used interchangeably herein, refer to any protein to which the affinity peptide is fused for the purpose of purification or immobilization.

As used herein, the term "fusion protein" refers to the protein hybrid comprising a metal ion affinity peptide and a fusion partner polypeptide.

As used herein, the term "metal ion" refers to any metal ion for which the affinity peptide has affinity and that can be used for purification or immobilization of a fusion protein. Such metal ions include, but are not limited to, $Ni^{+2}$, $Co^{+2}$, $Fe^{+3}$, $Al^{+3}$, $Zn^{+2}$ and $Cu^{+2}$. As used herein, the term "hard metal ion" refers to a metal ion that shows a binding preference for oxygen. Hard metal ions include $Fe^{3+}$, $Ca^{2+}$, and $Al^{3+}$. As used herein, the term "soft metal ion" refers to a metal ion that shows a binding preference of sulfur. Soft metal ions include $Cu^+$, $Hg^{2+}$, and $Ag^+$. As used herein, the term "intermediate metal ion" refers to a metal ion that coordinates nitrogen, oxygen, and sulfur. Intermediate metal ions include $Cu^{2+}$, $Ni^{2+}$, $Zn^{2+}$, and $Co^{2+}$.

As used herein, the terms "adsorbent" or "solid support" refer to a chromatography or immobilization medium used to immobilize a metal ion.

DESCRIPTION OF THE SPECIFIC EMBODIMENTS

Water-soluble metal ion affinity compounds and methods for using the same are provided. The subject compounds include an aspartate based metal chelating ligand bonded to a water-soluble polymeric substrate, where the ligand is complexed with a metal ion. In certain embodiments, the subject compounds further include a member of a signal producing system, e.g., a directly or an indirectly detectable label moiety. Also provided are water-insoluble supports having the subject compounds present on, e.g., immobilized on, at least one surface thereof. The subject compounds find use in a variety of different applications, including analyte detection and analyte purification applications.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a protein" includes a plurality of such proteins and reference to "the labeling method" includes reference to one or more labeling methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

As summarized above, the subject invention provides water-soluble polymeric metal ion affinity compounds, as well as methods for the use and kits that include the subject compounds. In further describing the subject invention, the subject compounds are described first in greater detail, followed by a review of representative methods in which they find use and a review of the kits that include the subject compounds.

Water-Soluble Polymeric Metal Ion Affinity Compounds

As summarized above, the present invention provides water-soluble metal ion affinity compositions. The subject water-soluble metal ion affinity compositions are characterized by having an aspartate based metal ion chelating ligand bonded to a water-soluble polymeric substrate. By aspartate based metal ion chelating ligand is meant a ligand that is synthesized from an aspartic acid, e.g., L-aspartic acid. In certain embodiments, the aspartate based metal ion, chelating ligand is a tetradentate ligand. By tetradentate ligand is meant that the ligand chelates a metal ion by occupying up to four, and typically four, coordination sites of a metal ion. For example, where a given metal ion has six coordination sites, four of them can be occupied simultaneously by the subject tetradentate ligands.

In certain embodiments, the aspartate based metal ion chelating ligand is an alkylaspartate ligand, generally a lower alkylaspartate ligand, such as 1 to 6, typically a 1 to 4 carbon atom alkylaspartate ligand, where the alkyl moiety may or may not be substituted. Representative alkylaspartate ligands of interest include, but are not limited to: carboxymethylated aspartate ligand, carboxyethylated aspartate ligand, etc.

As summarized above, the subject compounds are water-soluble metal ion chelating resins that include a water-soluble carrier matrix, optionally a spacer, and a moiety that comprises a metal ion, e.g., an organic ligand that immobilizes a metal ion. As the subject compositions are water-soluble, they are soluble in aqueous media, i.e., they go into solution in aqueous media.

Water soluble polymeric substrates or carrier matrices may vary significantly in terms of composition and weight, so long as they are water-soluble and are compatible with the aspartate based chelating ligand and the application in which the water soluble compound is to be employed. Water-soluble polymeric substrates or carrier matrices of interest include, but are not limited to: polysaccharides, e.g., dextrans, cross-linked dextrans, agarose, polyethylene glycol, polyethylene iminepolystyrenes; nylon; polyacrylamides; etc. As such, polymer matrices, e.g., polystyrene (as in microtiter plates), nylon (as in nylon filters), SEPHAROSE™ (Pharmacia, Uppsala, Sweden) or the like, can be used with the subject invention.

The molecular weight of a polymeric substrate component of a given water-soluble compound according to the subject invention may vary greatly, e.g., from about 300 daltons to 2,000,000 daltons or greater, so long as the polymeric substrate is water soluble. In many embodiments the average molecular weight of the polymeric substrate of a population of compounds according to the subject invention falls within the range from about 10 to about 100 kd, e.g., from about 10 to about 50 kd, including but not limited to from about 15 to about 30 kd.

In the subject compounds, the above described water-soluble polymeric substrate component is bonded, optionally through a linking group, to the above described aspartate based metal ion chelating ligand. In the subject compounds, the ligand may be bonded, usually covalently bonded, to the carrier matrix or substrate either directly or through a linking group. Where linking groups are employed, such groups are chosen to provide for covalent attachment of the ligand to the substrate through the linking group. Linking groups of interest may vary widely depending on the nature of the substrate and ligand moieties. The linking group, when present, should preferably be biologically inert. A variety of linking groups are known to those of skill in the art and find use in the subject soluble metal ion chelating compounds. In many embodiments, the size of the linker group, when present, is generally at least about 50 daltons, usually at least about 100 daltons and may be as large as 1000 daltons or larger, but generally will not exceed about 500 daltons and usually will not exceed about 300 daltons. Generally, such linkers include a spacer group terminated at either end with a reactive functionality capable of covalently bonding to the substrate or ligand moieties. Spacer groups of interest include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject molecules include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The aspartate based ligands are typically bonded to the polymeric substrates at a ratio of ligand to residue, e.g., glucose unit, that provides for acceptable characteristics, where the ratio of ligand to polymeric residue often ranges from about 1 ligand for every about 1 to 100 residues, e.g., from about 1 ligand for every about 5 to 50 residues, including 1 ligand or every about 10 to about 20 residues.

In certain embodiments, the aspartate based metal ion chelating ligands of the subject water-soluble metal ion chelating compositions are complexed with, i.e., charged with, a metal ion. In other words, in certain embodiments a metal ion is chelated by the tetradentate, e.g., carboxymethyl aspartate, ligand component of the subject compounds.

A variety of different types of metal ions may be complexed to the ligands of the subject compounds. Metal ions of interest can be divided into three categories (hard, intermediate and soft) based on their preferential reactivity towards nucleophiles. Hard metal ions of interest include, but are not limited to: $Fe^{3+}$, $Ca^{2+}$ and $Al^{3+}$ and like. Soft metal ions of interest include, but are not limited to: $Cu^+$, $Hg^{2+}$, $Ag^+$, and the like. Intermediate metal ions of interest include, but are not limited to: $Cu^{2+}$, $Ni^{2+}$, $Zn^{2+}$, $Co^{2+}$ and the like. In certain embodiments, the metal ion that is chelated by the ligand is $Co^{2+}$. In certain embodiments, the metal ion of interest that is chelated by the ligand is $Fe^{3+}$. Additional metal ions of interest include, but are not limited to: $Eu^{3+}$, $La^{3+}$, $Tb^{3+}$, $Yb^{3+}$, and the like.

In certain embodiments, the water-soluble metal ion affinity composition has the following structure:

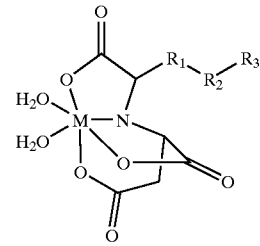

wherein:
M=metal ion;
$R_1$=a linking arm connecting the methylene carbon atom of the carboxymethyl group of CM-Asp with $R_2$;
$R_2$=a functional linking group that along with CM-Asp linking arm R1 is connected to $R_3$; and
$R_3$=a water-soluble polymeric substrate, which may have one or more additional residues bonded ligands of the same or different, but usually the same, structure.

Of particular interest in many embodiments are the water-soluble metal ion affinity compositions that are soluble versions or soluble derivatives of the metal ion chelating compositions disclosed in U.S. Pat. Nos. 6,242,581 and 5,962,641 and U.S. patent application Ser. No. 09/920,684, now abandoned, published as US 2002/0019496; the disclosures of which are herein incorporated by reference.

In certain embodiments, (e.g., where the compounds are designed for use in analyte detection applications as described in greater detail below), the subject water-soluble metal ion affinity compounds include a member of a signal producing system. By signal producing system is meant a system of one or more reagents that work to provide a detectable signal, where the member of the single producing system that is included in the compound is referred to herein as the signal producing system moiety. The signal producing system moiety may be directly or indirectly detectable, i.e., the metal ion affinity composition may include a label moiety that may be a directly detectable or indirectly detectable label. By "include" is meant that the moiety is bound to the affinity compound, where the bond may be covalent or non-covalent.

Examples of labels that permit direct measurement of the metal ion affinity composition include variety of different labels, such as fluorescent labels, isotopic labels, particulate labels, etc. For example, suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), cyanine dyes, e.g. Cy5, Cy3, BODIPY dyes, e.g. BODIPY 630/650, Alexa542, etc. Suitable isotopic labels include radioactive labels, e.g. $^{32}P$, $^{33}P$, $^{35}S$, $^{3}H$. Other suitable labels include size particles that possess light scattering, fluorescent properties or contain entrapped multiple fluorophores.

Examples of labels which permit indirect measurement include enzymes where a substrate may provide for a colored or-fluorescent product. For example, the metal ion affinity composition may be labeled with a covalently bound enzyme, such as horse radish peroxidase (HRP), capable of providing a detectable product signal after addition of suitable substrate. Enzymes finding use include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, glucose oxidase, lactate dehydrgenase and acetylcholinesterase. Substrates for such enzymes include, but are not limited to: chromogenic substrates, where suitable substrates include, but are not limited to: o-phenylenediamine (OPD), 3,3',5,5'-tetramethylbenzidine (TMB), 3,3'-diaminobenzide tetrahydrochloride (DAB) and the like.

The signal producing system and label components thereof may be part of a multi-stage system. One example of a two-stage system is a system where the affinity composition is conjugated to first member of a specific binding pair, e.g., biotin, haptens, etc., which first member has a high affinity for a second member of a binding pair, e.g. avidin, streptavidin, specific antibodies, etc. The second binding pair member, i.e., binding partner, may be conjugated to a label moiety, which may or may not be directly detectable, e.g., an enzymatic label capable of converting a substrate to a chromogenic product, a fluorescent label, and isotopic label, etc. Thus, instead of covalently binding the enzyme to the metal ion affinity composition, it may be modified, to comprise a first member of specific binding pair which specifically binds with a second member of the specific binding pair that is conjugated to the enzyme, e.g., it may be covalently bound to biotin and the enzyme conjugate to streptavidin.

In certain embodiments, the subject water-soluble compounds are immobilized on a surface of an insoluble support or substrate, i.e., a solid support. In certain embodiments, the solid support or substrate is a planar substrate. In these embodiments, the substrates may be fabricated from a variety of materials. In certain embodiments, the materials are ones that are transparent to visible and/or UV light. In certain embodiments, the materials are flexible substrates, where flexible materials of interest include: nylon, both modified and unmodified, nitrocellulose, polypropylene, and the like, where a nylon membrane, as well as derivatives thereof. In certain embodiments, the materials are rigid substrates, where specific rigid materials of interest include: glass; plastics, e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g. nylon or nitrocellulose, etc.

Solid supports of interest also include compositions that are made up of a plurality of individual solid supports (i.e., a plurality of solid supports that are physically unattached to other solid supports.) In these embodiments, the solid supports are frequently beads. Beads can be any shape, e.g., spherical, irregular, cuboidal, and the like. Beads that are suitable for use in the present invention can comprise any material that is stable to the chemistry used to attach compounds to the bead, including, but not limited to, latex, polystyrene, polyethylene/polypropylene, polycarbonate, polymethylmethacrylate, chloromethylpolystyrene-1%-divinylbenzene, silica, porous glass, aluminosilicates, borosilicates, metal oxides such as alumina and nickel oxide, and various clays. Included in the term "polystyrene" are polymers that have been substituted to some extent with substituents that are not capable of reaction under the conditions used for synthesis, including, for example, alkyl substituents such as methyl, ethyl, propyl, butyl, alkoxy substituents, etc. In order to increase the stability and insolubility in organic solvents, polystyrene resins that have been cross-linked by co-polymerization with divinyl benzene or butadiene are also used. Beads that are suitable for use also include magnetic beads.

Exemplary beads that can be employed include cellulose beads, pore-glass beads, silica gel, polystyrene beads, particularly polystyrene beads cross-linked with divinylbenzene, grafted copolymer beads such as polyethyleneglycol, polystyrene, polyacrylamide beads, latex beads, dimethylacrylamide beads, particularly cross-linked with N,N'-bis-acryloyl ethylene diamine and comprising N-t-butoxycarbonyl-β alanyl-N'-acryloyl hexamethylene diamine composites, such as glass particles coated with a hydrophobic polymer such as cross-linked polystyrene or a fluorinated ethylene polymer to which is grafter linear polystyrene; and the like. General reviews of useful solid supports (particles) that include a covalently-linked reactive functionality can be found in Atherton et al., Prospectives in Peptide Chemistry, Karger, 101–117 (1981); Amamath et al., Chem. Rev., 77:183–217 (1977); and Fridkin, The Peptides, Vol. 2, Chapter 3, Academic Press, Inc., (1979), pp. 333–363.

In the above embodiments, the subject water-soluble metal ion affinity compounds are immobilized onto a surface of the solid support. The compounds may be immobilized through either covalent or non-covalent bonding, as is known in the art. In certain embodiments, the compounds are adsorbed to the surface of the solid support.

Methods of Fabrication

The subject water-soluble metal ion affinity compounds may be prepared using any convenient protocol. In many embodiments, the method includes generation of a water insoluble metal ion affinity composition, e.g., gel, followed by degradation of the water insoluble composition to produce the final water-soluble product. The initial water insoluble metal ion affinity composition can be prepared using any convenient protocol. Representative protocols are disclosed in U.S. Pat. Nos. 6,242,581 and 5,962,641; the disclosures of which are herein incorporated by reference.

The initial water insoluble composition, e.g., gel, is water solubilized using any convenient protocol. Typically, the water solubilization protocol includes breaking up, disrupting or degrading the polymeric backbone of the water insoluble composition to produce water-soluble fragments of the initial composition. In many embodiments, this solubilization step includes breaking bonds between residues in the polymeric backbone of the initial water insoluble composition, e.g., by hydrolysis. Bonds can be broken using any convenient protocol, including contacting with a chemical hydrolyzing agent, contacting with an enzyme that hydrolyzes the backbone, e.g., dextranase, where the backbone is dextran, etc. A representative protocol is included in the experimental section, below. The bonds may also be broken mechanically, e.g., by subjection to shearing or other mechanical disruption forces.

The prepared water-soluble metal ion affinity compounds may be modified in a number of different ways, as may be desired. For example, where the subject compounds are labeled, any convenient protocol for labeling the compounds may be employed, including covalently bonding a label to the compound, e.g., through a diamine linker, etc., where a number of different protocols will be readily apparent to those of skill in the art and representative protocols are provided below.

Utility

The subject water-soluble metal ion affinity compositions find use in a number of different applications. Such applications include both purification and analyte detection applications. Each of these applications is now described in greater detail below.

Purification Applications

One type of application in which the subject water-soluble metal ion affinity compositions find use is purification. Specifically, the subject water-soluble metal ion affinity compounds find use in the purification of analytes that have an affinity for a chelated metal ions, e.g., chelated metal ions in a 2+ oxidation state with a coordination number of 6. The term purification is used broadly to refer to any application in which the analyte (i.e., target molecule) is separated from its initial environment, e.g., sample in which it is present, and more specifically the other components of its initial environment. In the subject purification applications, the protocol employed generally includes: contacting a fluid sample that includes the analyte of interest with the water soluble metal ion affinity compound under conditions sufficient for any analytes having affinity for the chelated metal ion to bind to the metal ion component of the water soluble metal ion affinity compound. In other words, the metal ion affinity composition and sample are combined under conditions sufficient to produce complexes between the analyte and the water-soluble compound in a resultant mixture. The soluble metal ion affinity composition may be free in solution or bound to an insoluble support, e.g., a bead, plate, well of a microtitre plate, etc, as described above.

Following this initial step, any resultant complexes are separated from the remainder of the initial sample. Separation may be achieved in a number of different ways, including two-phase separation protocols, separation based on weight, e.g., centrifugation protocols, electrophoretic protocols, etc; chromatographic protocols, etc.

Analytes that may be purified according to the subject methods include both phosphorylated compounds and metal ion affinity peptide tagged compounds. In many embodiments, the analytes of interest include a metal ion affinity tag, e.g., they are fusion proteins having a metal ion affinity tag domain, where particular metal ion affinity tags of interest include tags that have one or more histidine residues, e.g., poly-his containing affinity peptides. Representative metal ion affinity peptides of interest include those described in U.S. Pat. Nos. 4,569,794 and 5,594,115, as well as pending U.S. patent application Ser. No. 09/858,332 published as U.S. 20020164718; the disclosures of which are herein incorporated by reference.

In certain embodiments, the affinity peptide portion is a histidine-rich polypeptide sequence with a general sequence: $(XHYZ)_n$, wherein X and Y=any amino acid except histidine, Z=any amino acid, and n=2 or more. In yet other embodiments, the affinity peptide comprises a peptide of the formula $(His-X_1-X_2)_{n1}-(His-X_3-X_4-X_5)_{n2}-(His-X_6)_{n3}$, wherein each of $X_1$ and $X_2$ is independently an amino acid with an aliphatic or an amine side chain, each of $X_3$, $X_4$, $X_5$ is independently an amino acid with a basic or an acidic side chain, each $X_6$ is an amino acid with an aliphatic or an amide side chain, n1 and n2 are each independently 1–3, and n3 is 1–5. In some embodiments, the affinity peptide has the amino acid sequence NH$_2$-His-Leu-Ile-His-Asn-Val-His-Lys-Glu-Glu-His-Ala-His-Ala-His-Asn-COOH. In certain embodiments, the affinity peptide has the formula (His-Asn)$_n$, where n=3 to 10. In one particular embodiment, n=6. In certain embodiments, the affinity peptide has the formula $(His-X_1-X_2)_n$, wherein each of $X_1$ and $X_2$ is an amino acid having an acidic side chain, and n=3 to 10. In one embodiment, the affinity peptide comprises the sequence (His-Asp-Asp)$_6$. In another embodiment, the affinity peptide comprises the sequence (His-Glu-Glu)$_6$. In a further embodiment, the affinity peptide comprises the sequence (His-Asp-Glu)$_6$. These affinity peptides and methods for making analytes, e.g., fusion proteins, tagged with the same are further described in U.S. patent application Ser. No. 09/858,332, filed on May 15, 2001 and titled "Metal Ion Affinity Tags And Methods Of Use Thereof"; the disclosure of which is herein incorporated by reference.

In certain embodiments, following separation of the complexes from the remainder of the initial sample, the analyte is separated from the water-soluble metal ion affinity component. The analyte may be separated from the metal ion affinity component using any convenient protocol, where suitable protocols include changing the conditions, e.g., salt concentration etc, of the environment to achieve dissociation of the analyte from the chelated metal ion, where suitable conditions for achieving dissociation are known to those of skill in the art, particularly with knowledge of IMAC technology and more particularly elution of bound proteins from IMAC resins. See the above patents that are incorporated by reference for representative protocols that can be employed to achieve dissociation.

Specific representative purification applications in which the subject water-soluble metal ion affinity compositions find use include: (1) purification by two-phase separation protocols, e.g., of phosphorylated proteins, of metal ion affinity peptide, e.g., poly-histidine, etc; (2) solid support based purification applications, where the solid supports, e.g., glass, plastic, magnetic etc., surfaces, are coated with the subject water soluble compounds for purification of analytes having affinity therefore, e.g., polyhystidine or phosphorylated proteins; and the like.

In representative two phase separation protocols, a system made up of two aqueous solution phases or liquids that separate from each other upon standing, e.g., are immiscible, and in which the subject water-soluble metal ion affinity compounds have a distribution coefficient that is not equal to 1 is employed. For example, a two phase system made up of a salt buffer liquid and a polyethylene glycol liquid may be employed, where the subject water soluble metal ion affinity compounds have a distribution coefficient between the salt solution and the polyethylene glycol that is not equal to 1, since the subject water soluble metal ion affinity compounds favor the polyethylene glycol phase and are therefore present in the polyethylene glycol phase at a higher concentration than they are in the salt buffer phase following equilibrium establishment. In using such systems, the sample containing the analyte to be purified and the subject water soluble metal ion affinity compounds are added to the two phase system, which is then thoroughly mixed or agitated. The resultant mixture is then allowed to set or rest for a period of time sufficient for the immiscible phases, to separate. The phase that favors the subject water soluble metal ion affinity compounds (or at least a portion thereof that has a high concentration of the water soluble metal ion affinity compounds and any analytes complexed therewith, such as the interface portion of the two phase system) is then separated from the remainder of the system, and the analyte of interest to be purified is harvested from the separated phase or portion thereof. The analyte may be further isolated by separating it from the water-soluble metal ion affinity compound to which it is complexed, as described above. The above protocol may be repeated one or more additional times in order to obtain an analyte preparation of desired purity.

In yet other embodiments, the subject water-soluble metal ion affinity complexes are immobilized on a solid support and employed as solid support bound affinity reagents for purifying one or more analytes from a sample. In such embodiments, the solid supports having the subject water soluble metal ion affinity compounds immobilized on a surface thereof are contacted with the sample so that any analytes having affinity for the metal ion affinity compounds bind to the surface immobilized metal ion affinity compounds. The resultant solid support bound complexes are then separated from the remainder of the mixture to obtain purified analyte, which can then be further separated from the solid support immobilized water soluble metal ion affinity compounds, as described above.

Analyte Detection Applications

Also provided are analyte detection applications, in which the subject water-soluble metal ion affinity compositions are employed to detect the presence of an analyte in a sample. The analyte is generally an analyte having affinity for a chelated metal ion, e.g., a metal ion in a 2+oxidation state with a coordination number of 6, as described above. Representative analytes of interest include, but are not limited to: fusion proteins tagged with a metal ion affinity peptide, such as a poly his containing peptide, as described above; phosphorylated proteins, etc.

In analyte detection applications, a sample suspected of containing an analyte of interest, i.e., a sample to be screened or assayed, is contacted with a water-soluble metal ion affinity-compound according to the subject methods, where the subject water-soluble metal ion affinity compound typically includes a member of a signal producing system, as described above. Contact of the water-soluble metal ion affinity compound and the assayed sample occurs under conditions sufficient for complexes to be produced between the water-soluble metal ion affinity compounds and analytes having a binding affinity therefore in the sample. As such, contact occurs for a period of time and at a temperature that provides for binding of analytes and water-soluble metal ion affinity compounds that having binding affinity for each other. Suitable temperatures and time durations are readily determined by those of skill in the art.

Following contact, the resultant contacted mixture is screened for the presence of any binding complexes made up of analytes and water-soluble metal ion affinity compounds. In other words, the presence or absence of analyte/water soluble metal ion affinity compound complexes in the sample contacted mixture is determined. The binding complexes of interest are detected using any convenient protocol, including but not limited to: spectrophotometric, fluorimetric or by visual means. In certain embodiments, a reagent may be added to the contacted mixture to provide for detection. For example, where enzyme labels are employed, the enzyme is reacted with an appropriate substrate, preferably a chromogenic substrate, in such a manner as to produce a chemical moiety which can be detected, for example, by spectrophotometric, fluorimetric or by visual means.

In certain embodiments, the detection step as summarized above occurs after a separation step, in which the binding complexes of interest are first separated from the remainder of the contacted mixture, including unbound water-soluble metal ion affinity compounds. Any convenient separation protocol may be employed, where representative separation protocols are provided above.

The final step is to relate the detected signal generated from the detectably labeled metal ion affinity/analyte complexes to the presence of the corresponding analyte in the fluid sample that has been assayed. The detected signal can be used to qualitatively determine whether or not the analyte of interest is present in the sample that has been assayed. Alternatively, the detected signal can be used to quantitatively determine the amount of the analyte of interest in the assayed sample. Quantitative determination is generally made by comparing a parameter of the detected signal, e.g., intensity, with a reference value (such as the intensity of signal generated from a known amount of label).

As such, the above process can be used to detect the presence of one or more analytes in a fluid sample, either quantitatively or qualitatively.

Specific representative analyte detection applications in which the subject water-soluble metal ion affinity compositions find use include: (1) detection of analytes having affinity for immobilized metal ions, e.g., phosphorylated proteins, metal ion affinity peptide tagged proteins, etc., in homogenous (e.g., liquid phase) and heterogenous (e.g., solid phase, such as array) applications; (2) detection of protein—protein interactions (e.g., where one employs a phosphorylated or poly-histidine tagged protein as bait); (3) amplification reactions; etc.

In homogenous detection applications, the water-soluble metal ion affinity compounds and the analyte to be detected are both present in solution phase when contacted in order to produce binding complexes. The resultant solution phase produced binding complexes are then detected using any convenient protocol, e.g., by separating the resultant complexes from the remainder of the initial mixture, (for example by using a resin that has affinity for the subject water soluble metal ion affinity compounds); by employing a single producing system that provides for differential signal depending on whether or not the water-soluble metal ion affinity compound is complexed with an analyte, etc.

In heterogenous detection applications, one of the water-soluble metal ion affinity compound and the analyte to be detected is immobilized on a solid support, such that during the contact step, one of these two components is immobilized on a solid support and the other becomes immobilized on the solid support by virtue of its binding to the solid support immobilized component. For example, in certain heterogenous applications, the analyte of interest is immobilized onto a surface of the solid support. In yet other embodiments, the water-soluble metal ion affinity compound is immobilized on the surface of a solid support.

In a particular application of interest, the subject water-soluble metal ion affinity compounds are employed in array based protein—protein interaction applications, analogous to those described in U.S. Pat. No. 6,197,599; the disclosure of which is herein incorporated by reference. For example, in such applications, one can employ a planar support that is coated with a water-soluble metal ion affinity compound, as described above. Onto this planar support can be deposited recombinantly produced metal ion affinity tagged fusion proteins to produce an array of spatially addressable tagged fusion proteins. The resultant array can then be contacted with a second labeled population of proteins, and any resultant surface bound complexes between the second and first populations can be detected to readily identify protein—protein interactions. Additional information regarding the nature of the proteins in the identified protein—protein interactions may be obtained, e.g., by contacting the resultant array with a second population of solution phase water-soluble metal ion affinity compounds charged with a metal ion that complexes with a certain type of protein, e.g., phosphorylated proteins. Various modifications of the above representative schemes will be readily apparent to those of skill in the art and are considered to be within the broad scope of analyte detection applications claimed below.

In certain of the above applications, it may be desirable to covalently bond a protein complexed with a metal ion affinity ligand compound of the subject invention to the metal ion affinity ligand. One convenient protocol for producing a covalent bond between the two members of such a complex would be to oxidize hydroxyl moieties present on the water soluble polymer component of the metal ion affinity compound, where the resultant oxidized moieties, e.g., —CHO moieties, could then covalently bond to primary amines present on the complexed proteins. For example, an existing population of 6×His and poly-histidine tagged proteins array in which the tagged proteins are immobilized onto the surface of a metal ion affinity compound coated substrate can be covalently bound to the substrate by oxidation of the chelated polymer on the solid surface, followed by formation of Schiff bonds with the N-terminal $NH_2$ groups of the polypeptides (which for the majority of the His-tagged proteins is in close proximity of the tag) and subsequent reduction of the bonds to a single covalent bond by reducing reagent. Such a protocol can be used in the synthesis of peptide arrays, where one desires a covalent attachment of a probe peptide to the surface of a solid support.

The subject soluble metal ion affinity reagents also find use in signal amplification reactions, where the subject reagents are members of an amplification signal producing system, which system typically includes one or more additional reagents, e.g., metal ion affinity tagged labels, including both directly and indirectly detectable labels, etc. Representative amplification applications of interest include those provided in more detail in the Experimental section, below. Such applications include, but are not limited to: amplification of signals from array based applications, application of signals from gel-based applications (e.g., those employing SDS gels), etc.

Kits and Systems

As summarized above, also provided are kits and systems for use in practicing the subject methods. The kits and systems at least include the subject water-soluble metal ion affinity compounds, as described above. The kits and systems may also include a number of optional components that find use in the subject methods. Optional components of interest include a signal producing system or components thereof, e.g., chromogenic substrates, etc. In many embodiments of the subject kits, the kits will further include instructions for practicing the subject methods or means for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

The following examples are offered by way of illustration and not by way of limitation.

EXPERIMENTAL

I. Protocol for Preparation of Soluble CM-Asp-dextran Derivatives (TALON-Dextran)

A. Swell 5 g of Sephadex G-150 SF (Sigma G-150-50) in Milli Q water for 24 hours. Approximate swelling volume~100 mL. Use 250 to 300 mL of Milli Q water.

B. TALON-Sephadex G150

1. Epoxy Activation of Sephadex G-150

Remove excess water from the swollen beads by vacuum filtration. 100 g of suction-dried Sephadex G-200 are transferred to 1 L conical bottle, containing 100 mL of 2 M NaOH, 5 mL of Epichlorohydrin, 190 mg of $NaBH_4$ and 100 mL of Milli Q water. The mixture is left on a shaker at RT. After 4 hours fresh 20 mL of epichlorohydrin are added to the mixture and the reaction is allowed to proceed for total of 20 hours.

2. Coupling of Aspartic Acid

The Epoxy-activated Sephadex is washed extensively with Milli Q water until pH=8 is detected in the flow through. Then the gel (100 g) is transferred with 125 mL of $Na_2CO_3$ to a 2 L conical bottle. 250 mL of 1.0 M $Na_2CO_3$ containing 10 g of aspartic acid (pH corrected to >12 with 0.2 M NaOH) are added and the coupling is allowed to proceed for 16 hours. The gel is washed with Milli Q water—to pH=8.

3. Carboxy-Methylation

The Asp-Sephadex G 150 is carboxymethylated. Wash Aspartate-Sephadex with 1×700 mL 10% $Na_2CO_3$. Suction dry. Dissolve 11.25 g NaOH in 150 mL $H_2O$ with mechanical stirring in a 250 ml flask. Cover solution and place in refrigerator to cool overnight. Remove NaOH solution from refrigerator and place in an ice bath. Add 37.5 g bromoacetic acid (MW 139) in 7.5 g increments, with stirring. Monitor temperature of solution during the addition; the temperature should be no higher than 30° C. at the end of the addition. Before proceeding, test the pH of the solution. If the pH is <7, add NaOH pellets, 0.5 g at a time, being careful not to let the temperature exceed 30° C., until the solution pH is >7. Carefully add 8.25 g $Na_2CO_3$ (MW 106) with stirring, and remove the ice bath; the $Na_2CO_3$ will go completely into solution as the solution warms. Adjust pH to the range 10.0–10.1 with conc. HCl or conc. NaOH, using a standardized pH meter. Set up a 10 gallon bucket with mechanical stirring. Transfer the washed and suction dried resin to the flask. Transfer bromoacetic acid solution to the flask and stir at ambient for at least 43 hours. Collect resin by filtration. Wash thoroughly with 6×100 mL MilliQ water, 1×700 mL 10% acetic acid, and 18×100 mL MilliQ water. The first two water washes must be disposed of in the aqueous waste container. In the final MilliQ water washing step, you must continue washing with water until pH 6 by litmus (unless the pH of the MilliQ water is <6, in which case you must wash until the pH of the filtrate is the same as that of the water). Suction dry.

4. Metal Ion Content 2 g of the final swollen TALON-Sephadex G150 are charged with 10 mL of 50 mM $CuSO_4$ in Milli Q water, washed multiple times with Milli Q water and vacuum dried in a pre-weighted tube (Do not use temperature higher than 40° C. during the concentration). The initial weight is subtracted from the final weight of the tube to determine the amount of the Sephadex. The metal ion content is determined according to the old TALON procedure (EDTA extraction) and reported in $\mu$mol Cu/mg dry Sephadex G 150 (target metal ion content is 1 $\mu$mol Cu/3.6 mg Sephadex G150 and higher).

C. Hydrolysis of TALON-Sephadex G50 (TALON-Dextran)

95 g of TALON-Sephadex G 150 are transferred to a 2 L conical bottle with 500 mL of 0.2 M Na-phosphate pH 6.0. The total volume of the mixture is adjusted to 1600 mL with Milli Q water. A sample of 1 mL is removed. 10 mL of 1.1 mg/mL Dextranase (~0.78 U) (SIGMA D-5884) is added and the mixture is left on rotary shaker (setting 5.5). After 24 hours of hydrolysis the reaction mixture is centrifuged at 5000×g. After centrifugation the supernatant is transferred to a new clean container. The TALON-Dextran solution is then incubated for 30 minutes at 100° C. and centrifuged again. After centrifugation the supernatant is transferred to a new clean container. The above protocol produces a Soluble TALON compound.

II. Modification of Soluble TALON Compound

A. Oxidation of Soluble TALON Compound 31 mg of dry soluble TALON compound as described above is dissolved in 0.5 mL of 800 mM sodium citrate pH 4.0 and 2 mL of DI water containing 10 mg of $NaIO_4$. Oxidation is carried out for 3 hours.

B. Modification of Oxidized Soluble TALON with $NH_2$—$C_2H_4$—$NH_2$

Excess $NaIO_4$ is then removed from the resultant oxidized Soluble TALON by SEC on PD-10 columns equilibriated with 20 mM Na-phosphate; 0.15 M NaCl pH 7.5. The eluate containing the oxidized dextran is then collected in a tube containing 6 mg of $NH_2$—$C_2H_4$—$NH_2$ (MW=60.10 (0.1 mM). The formation of Schiff bonds is allowed to proceed for 1 hour at RT and slow shaking. The unsaturated Schiff bonds are reduced by addition of 5 mg of $NaBH_4$. After 1 hour at RT, the samples are left for dialysis overnight against DI water to remove excess $NH_2$—$C_2H_4$—$NH_2$.

Analogous modifications can be made with $NH_2$-PEG-$NH_2$ or analogous compounds, which modifications find use in labeling protocols, where the soluble TALON product is labeled with a detectable label, e.g., through covalent attachment to the now present primary amine moieties.

C. Preparation of HRP-N-TALON Conjugate 9 mg horse radish peroxidase (HRP) (Boerhinger Mannheim 108090) is dissolved in 2.5 mL phosphate buffer (100 mM sodium phosphate, pH 7.2). 10 µl glutaraldehyde (50% glutaraldehyde (photographic grade)), is added and the resultant mixture is incubated for 1 hour at ambient temperature. The incubated product is then desalted against the phosphate buffer on a PD 10 column. One mL of the activated HRP is then placed into three tubes containing 5, 10, and 20 µl respectively of 0.5 M soluble TALON (2.5, 5 and 10 µm respectively). 0.5 mL is placed in a separate tube with 20µ ethanolamine. The mixtures are then incubated for four hours at ambient temperature. The resultant four variants are dialyzed against 1 L of 2 mM MOPS pH 7.5 for one hour at 4° C. followed by overnight dialysis against fresh 1 L of the same buffer at 4° C. The resultant variants are then dialyzed against 1 mM $COCl_2.7H_2O$ in 2 mM MOPS pH7.5 for 3 hours. The resultant variants are then dialyzed against 1 L of 2 mM MOPS pH 7.5 for two hours at 4° C. followed by overnight dialysis against fresh 1 L of the same buffer at 4° C.

III. Representative Applications of Soluble TALON Compounds

A. Detection of Printed Polyhistidine Proteins on Glass Slides by HRP-TALON Conjugates Serial dilutions of HAT-GFPuv-EK (HAT tagged Green fluorescent protein) are printed on a PIDTC slide using the protocol published in WO 02/25288. The resultant slide is blocked for one hour with BLOTTO, washed with 2×300 µl TST buffer, followed by 3×300 µl of 50 mM sodium phosphate; 0.25 M NaCl; 0.05% Tween 20 pH 7.0.

3 µl of HRP-TALON as described above is added to fresh 300 µl of 50 mM sodium phosphate; 0.25 M NaCl; 0.05% Tween 20 pH 7.0 present on the slide. The slide is carefully inverted at approximately a 15° angle to mix the HRP-TALON conjugate without leakage of the solution out of the frame. After 1 hour the unbound HRP-TALON is washed out with 5×300 µl of 50 mM sodium phosphate; 0.24 M NaCl; 0.05% Tween 20 pH 7.0. 300 µl of TMB substrate is added and the color reaction is allowed to proceed.

B. Detection of Phosphorylation

1. Preparation of the Metal Ion Affinity (MIA) Reagent

Soluble TALON-dextran (prepared as described earlier) is amino modified by oxidation with $NaIO_4$ and conjugation of $NH_2$-PEG-$NH_2$. The primary amines are utilized for conjugation of Biotin (Biotin-NHS ester). The Biotin-TALON-dextran is charged with Fe(III) and excess Fe(III) is removed by dialysis.

2. Application to Phosphorylation Detection on Arrays a. Protein extract is labeled by Cy5 dye. The extract is incubated with an antibody array. Non-bound protein is washed away. Fe(III)-TALON-Biotin-detxran is incubated with the array of bound antigens. Non bound Fe(III)-TALON-Biotin-detxran is washed away. Cy3-Streptavidin is incubated with the antigens/Fe(III)-TALON-Biotin-detxran: Non bound Cy3-Streptavidin is washed away. The slide is scanned in appropriate scanner. The ratio between the Cy5 and Cy3 signal is a relative measure for the level of phosphorylation of any specific antigen bound on the array. The relative phosphorylation level of two samples can be determined by comparing the internal Cy5/Cy3 ratios on the spot for two different arrays run with the two samples. This protocol has been employed to assay Jurkat and HeLa cell lines and relative differences between the levels of phosphorylation have been detected. The binding of the metal ion affinity reagent to the antigen has been shown to be specific by its removal from the spots with either phosphate or EDTA.

b. Multiplex Detection of Enzymatic Activity.

Non phosphorylated proteins are immobilized in an array format. The array is incubated with protein extract containing enzymes with phosphorylation activity. The protein extract is washed away. Fe(III)-TALON-Biotin-detxran is incubated with the array of bound antigens. Non bound Fe(III)-TALON-Biotin-detxran is washed away. Cy3-Streptavidin is incubated with the antigens/Fe(III)-TALON-Biotin-detxran. Non bound Cy3-Streptavidin is washed away. The slide is scanned and a profile of the phosphorylation enzymes is obtained. The profiles of two different samples can be compared. This procedure can be performed with the Ab array as a primary binder of the substrate proteins (e.g., labeled with Cy5), followed by de-phosphorylation with phosphatase and repeating the steps described above.

3. Application of Soluble TALON-dextran to Amplification of the Signal

A. A sample is biotinylated. It is applied to an Ab array. Non adsorbed material is washed away. Streptavidin (SA) is incubated with the array. Non bound SA is washed away. Co(II)-TALON-Biotin-dextran is incubated with the Ab array. Non bound metal ion affinity reagent is washed away. 6×His-Protein-6×His-Cy3 conjugate is incubated with the array. Non bound protein is washed away. The last-4 steps can be repeated multiple times to yield amplified signal.

B. In a variation of the signal amplification procedure described above, instead of using multiple layers of double His-tagged and labeled proteins with TALON-dextran, one can use any 6xHis-tagged enzyme that produces a fluorescent or chemiluminescent substrate.

A representative protocol is as follows:

1. Label biological sample with biotin
2. Apply sample to array (or SDS gel)
3. Wash non adsorbed material (or transfer protein bands to membrane, block membrane)
4. Apply Streptavidin (SA)/Biotin-Dextran-TALON or SA-Dextran-TALON
5. Wash excess TALON
6. Apply any 6xHis tagged enzyme (or chemically poly histidine modified glycoprotein enzyme)
7. Wash excess enzyme
8. Apply enzyme substrate
9. Wash away non converted substrate
10. Read signal It is evident from the above discussion and results that the subject invention provides an important new type of metal ion affinity reagent that finds use in a variety of different applications, including novel selective protein purification applications with additional selectivity, novel analyte detection applications, etc. As such, the subject invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A water-soluble polymeric metal ion affinity compound comprising:
   an aspartate based metal chelating ligand bonded to a water-soluble polymeric substrate, wherein said ligand is complexed with a metal ion.
2. The water-soluble polymeric metal ion affinity compound according to claim 1, wherein said water-soluble polymeric substrate is a polysaccharide.
3. The water-soluble polymeric metal ion affinity compound according to claim 2, wherein said polysaccharide is chosen from agarose and dextran.
4. The water-soluble polymeric metal ion affinity compound according to claim 1, wherein said metal ion is a hard metal ion.
5. The water-soluble polymeric metal ion affinity compound according to claim 4, wherein said hard metal ion is one of $Fe^{3+}$, $Ca^{2+}$ and $Al^{3+}$.
6. The water-soluble polymeric metal ion affinity compound according to claim 1, wherein said metal ion is an intermediate metal ion.
7. The water-soluble polymeric metal ion affinity compound according to claim 6, wherein said intermediate metal ion is one of $Co^{2+}$, $Ni^{2+}$, $Cu^{2+}$, or $Zn^{2+}$.
8. The water-soluble polymeric metal ion affinity compound according to claim 1, wherein said metal ion is a soft metal ion.
9. The water-soluble polymeric metal ion affinity compound according to claim 8, wherein said soft metal ion is one of $Cu^+$, $Hg^{2+}$ and $Ag^+$.
10. The water-soluble polymeric metal ion affinity compound according to claim 1, wherein said metal ion is $Co^{2+}$.
11. The water-soluble polymeric metal ion affinity compound according to claim 1, wherein said metal ion is $Fe^{3+}$.
12. The water-soluble polymeric metal ion affinity compound according to claim 1, wherein said aspartate based ligand is synthesized from an aspartic acid.
13. The water-soluble polymeric metal ion affinity compound according to claim 12, wherein said aspartate based ligand is a tetradentate ligand.
14. The water-soluble polymeric metal ion affinity compound according to claim 13, wherein said aspartate based ligand is an alkylated aspartate ligand.
15. The water-soluble polymeric metal ion affinity compound according to claim 14, wherein said alkylated aspartate ligand is a carboxymethylated aspartate ligand.
16. The water-soluble polymeric metal ion affinity compound according to claim 1, wherein said water-soluble polymeric metal ion affinity compound has the formula:

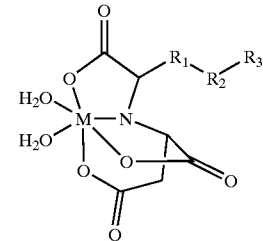

wherein:
   M=transition metal ion in a 2+ oxidation state with a coordination number of 6;
   $R_1$=a linking arm connecting the methylene carbon atom of the carboxymethyl group of Cm-Asp with $R_2$;
   $R_2$=a functional linking group through with CM-Asp linking arm R1 is connected to $R_3$; and
   $R_3$=a water-soluble polymeric substrate.
17. The water-soluble polymeric metal ion affinity compound according to claim 1, wherein said compound further comprises a member of a signal producing system.
18. The water-soluble polymeric metal ion affinity compound according to claim 17, wherein said member of a signal producing system is a directly detectable label.
19. The water-soluble polymeric metal ion affinity compound according to claim 17, wherein said member of a signal producing system is an indirectly detectable label.
20. A water insoluble substrate having a compound according to claim 1 present on a surface thereof.
21. A method of determining whether an analyte having affinity for a chelated metal ion is present in a sample, said method comprising:
   (a) contacting said sample with a water-soluble metal ion affinity compound according to claim 1 to produce a contacted mixture; and
   (b) screening said contacted mixture for the presence of complexes between said analyte and said water-soluble metal ion affinity compound to determine whether said analyte is present in said sample.
22. A method of separation an analyte having affinity for a chelated metal ion from other components of a sample, said method comprising:

(a) contacting said sample with a water-soluble metal ion affinity compound according to claim 1 to produce a contacted mixture; and (b) separating complexes between said analyte and said water-soluble metal ion affinity compound from other components in said contacted mixture to separate said analyte from other components of said sample.

23. A kit comprising:
(a) a water-soluble polymeric metal ion affinity compound according to claim 1; and
(b) instructions for using said water-soluble polymeric metal ion affinity compound to screen a sample for the presence of an analyte.

* * * * *